United States Patent [19]

Brighton et al.

[11] 4,430,999

[45] Feb. 14, 1984

[54] OSTEOGENESIS STIMULATING CATHODE ASSEMBLY FOR USE WITH AN INTERNAL FIXATION DEVICE

[75] Inventors: Carl T. Brighton, Malvern; Jonathan Black, King of Prussia, both of Pa.; Joyce K. Eyerly, White Bear Lake, Minn.

[73] Assignees: Trustees of the University of Pennsylvania; Zimmer, Inc.

[21] Appl. No.: 320,309

[22] Filed: Nov. 10, 1981

[51] Int. Cl.³ ............................................. A61N 1/18
[52] U.S. Cl. ................................. 128/419 F; 128/785
[58] Field of Search ................. 128/419 F, 642, 82.1, 128/784–786

[56] References Cited

U.S. PATENT DOCUMENTS

| | | | |
|---|---|---|---|
| 3,864,473 | 6/1973 | Wichhem et al. | 128/419 F X |
| 4,046,141 | 9/1977 | DeLuca | 128/642 |
| 4,195,367 | 4/1980 | Kraus | 128/419 F X |
| 4,306,564 | 12/1981 | Kraus | 128/419 F |

FOREIGN PATENT DOCUMENTS 3003758  8/1981  Fed. Rep. of Germany ...... 128/784

*Primary Examiner*—Lee S. Cohen
*Attorney, Agent, or Firm*—Ferguson, Baker, Whitham, Spooner & Kroboth

[57] ABSTRACT

A cathode assembly for use in conjunction with an internal fracture fixation device for the purpose of stimulating osteogenesis (bone growth) within a fracture site. The assembly is comprised of a carrier made from an implantable non-conductive material containing a cathode with a conductive cable leading from the cathode to the patient's electrical bone growth stimulating apparatus. The carrier is mountable on the fixation device for maintenance at the desired location. In a preferred embodiment, a sleeve carrier contains a plurality of ports which allow the current generated by the stimulating device to flow through the cable to the cathode where it is evenly distributed through the ports to the bone tissue. The sleeve can be slipped onto a fracture fixation device, such as a compression hip screw, and is located on the device such that the sleeve containing the cathode lies across the fracture site.

15 Claims, 13 Drawing Figures

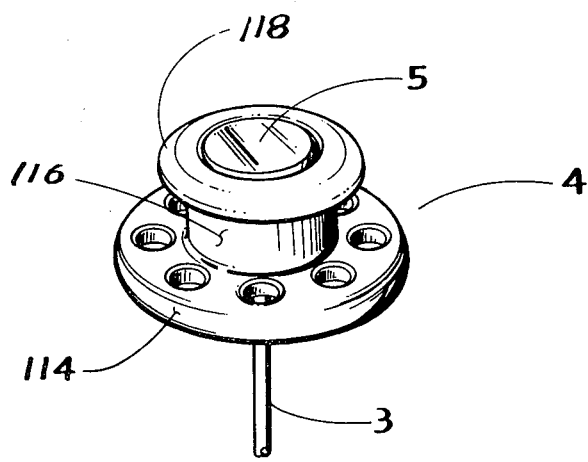
FIGURE 3
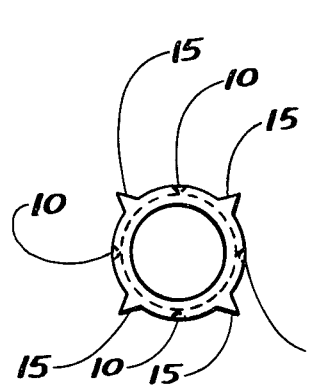 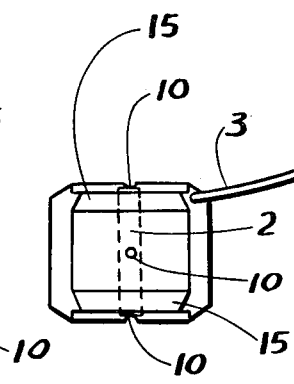 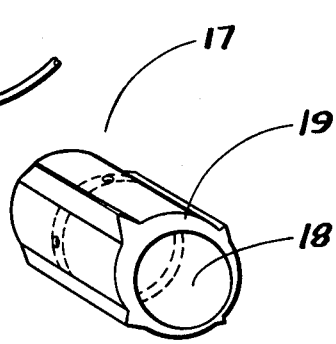
FIGURE 4a.     FIGURE 4b.     FIGURE 4c.
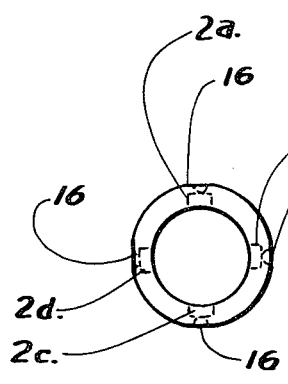 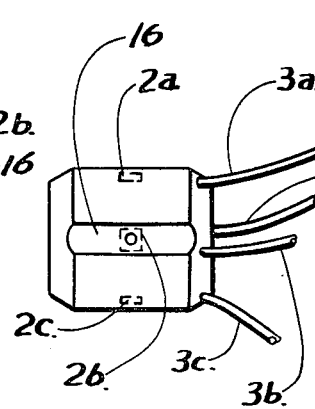 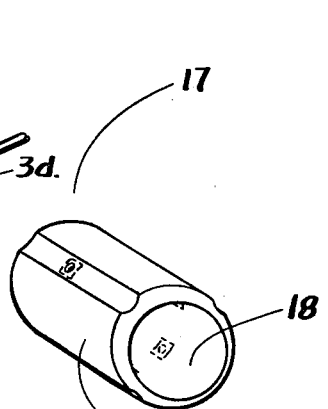
FIGURE 5a.     FIGURE 5b.     FIGURE 5c.

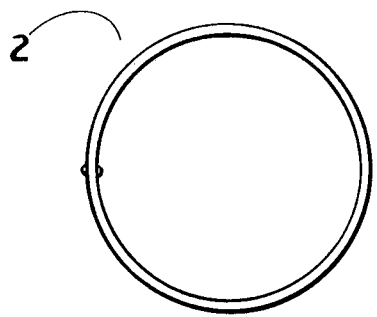
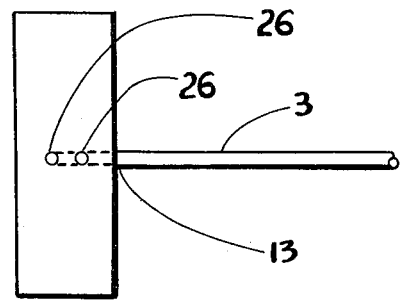
FIGURE 6  FIGURE 7
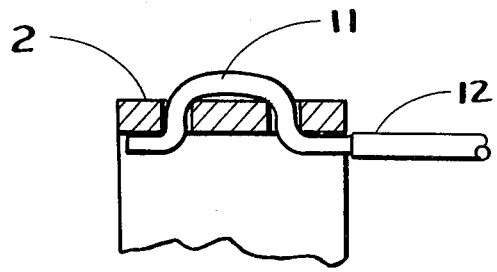
FIGURE 8
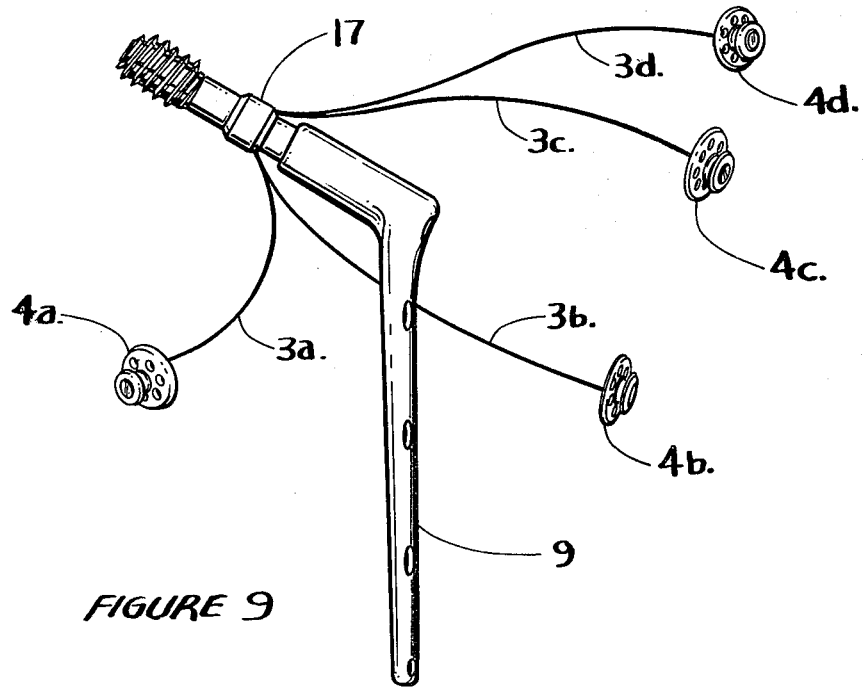
FIGURE 9

OSTEOGENESIS STIMULATING CATHODE ASSEMBLY FOR USE WITH AN INTERNAL FIXATION DEVICE

BACKGROUND OF THE INVENTION

The present invention relates generally to the electrical stimulation of bone for the promotion of osteogenesis or bone growth and relates specifically to the precise fixation of a cathode in the area where bone growth stimulation is desired.

U.S. Pat. No. 3,842,841 issued to Brighton, et al., Oct. 22, 1974 entitled "Constant Current Power Pack for Bone Healing and Method of Use," herein incorporated by reference, describes a system for promoting osteogenesis through the use of direct current of from five to twenty microamperes applied between a cathode inserted at the fracture or site of the bone defect and an anode applied to the skin, preferably by means of a surface electrode. The utilization of such a direct current from a cathode at the fracture site causes a higher than normal growth of bone cells in the vicinity of the cathode which is advantageous in expediting healing of a fracture or correction of a bone defect.

The above Brighton, et al. patent describes several types of cathodes which can be utilized to promote osteogenesis. One is a multi-strand stainless steel wire which is coated with an insulation, such as Teflon ® having a bare portion which is implanted at the fracture site. In order to get this cathode to the fracture site, a small incision must be made in the skin and the underlying tissue and the cathode is then placed in the vicinity of the fracture. The other electrode is a rigid stainless steel cathode pin which is coated with an electrical insulation except for a bare region at the end of the pin. No incision is necessary and the pin is merely pushed or driven through the skin and soft tissues into the vicinity of the fracture site.

One difficulty with such electrodes is that by virtue of the fact that they placed through soft, flexible tissue layers into the fracture site, movement of the externally projecting portion of the cathode may move or dislodge the cathode from the most desirable position. Many times, there is provided an internal fixation device for holding bony tissue in a predetermined fashion until sufficient bone growth has occurred to hold the fractured bones in the required relative position. In this instance, surgery is required in order to permit implantation of the internal fixation device. However, utilization of such a device in the past, while permitting ease of placement of the cathode, has not resulted in position maintenance of cathodes at the fracture location.

SUMMARY OF THE INVENTION

In view of the above and other difficulties encountered in prior art cathodes, it is one object of the present invention to provide a cathode assembly which is utilized in conjunction with an interal fixation device to accurately position the cathode assembly at a fracture site.

It is an additional object of the present invention to provide a device which is simple and convenient for a surgeon to use and which can be used in conjunction with orthopaedic fixation devices already familiar to the orthopaedic surgeon.

It is a further object of the present invention to provide a cathode assembly which will distribute electrical current evenly through a plurality of sites in the cathode assembly.

A still further object of the present invention is to provide a cathode assembly for use in conjunction with a compression hip screw which can be precisely located and maintained in position without requiring additional surgery other than that necessary to install the compression hip screw.

It is a still further object of the present invention to provide a cathode assembly which cooperates with any internal fixation device after installation to provide electrical osteogenesis stimulation without requiring additional surgical installation.

The above and other objects are achieved with the present invention which comprises a carrier device which is connectable to an internal fixation device. The cathode is mounted on the carrier which is subsequently attached to the internal fixation device after installation. In a preferred embodiment, the carrier is insulated, rendering it compatible with conducting fixation devices. A separate insulated conductor connects the cathode to an appropriate current generating device for providing the required stimulation current. In a preferred embodiment, the carrier is an insulated ring which slides over a compression hip screw after installation and is held in precise position by the hip screw. In a further preferred embodiment, the insulated carrier surrounds the cathode with the exception of a plurality of small openings or ports which permits the current to flow from the cathode through the surrounding tissues to the surface anode or any other suitable anode located on the patient.

BRIEF DESCRIPTION OF THE DRAWINGS

A more complete appreciation of the invention, and many of the attendant advantages thereof, will be readily apparent by reference to the accompanying drawings, wherein:

FIG. 3 is an enlarged perspective view of the percutaneous skin connector;

FIGS. 4a, 4b, and 4c are end, side, and perspective views respectively, of one embodiment of the cathode assembly;

FIGS. 5a, 5b, and 5c are end, side, and perspective views of a further embodiment of the present invention;

FIG. 6 is an enlarged view of one embodiment of the cathode;

FIG. 7 is a side view of the cathode embodiment shown in FIG. 6 further including the connecting cable;

FIG. 8 is a side cross-sectional view illustrating one means of attaching the cable to the cathode; and FIG. 9 is a perspective view of an alternate embodiment of the cathode assembly.

DETAILED DESCRIPTION OF PREFERRED EMBODIMENTS

Figure 2:
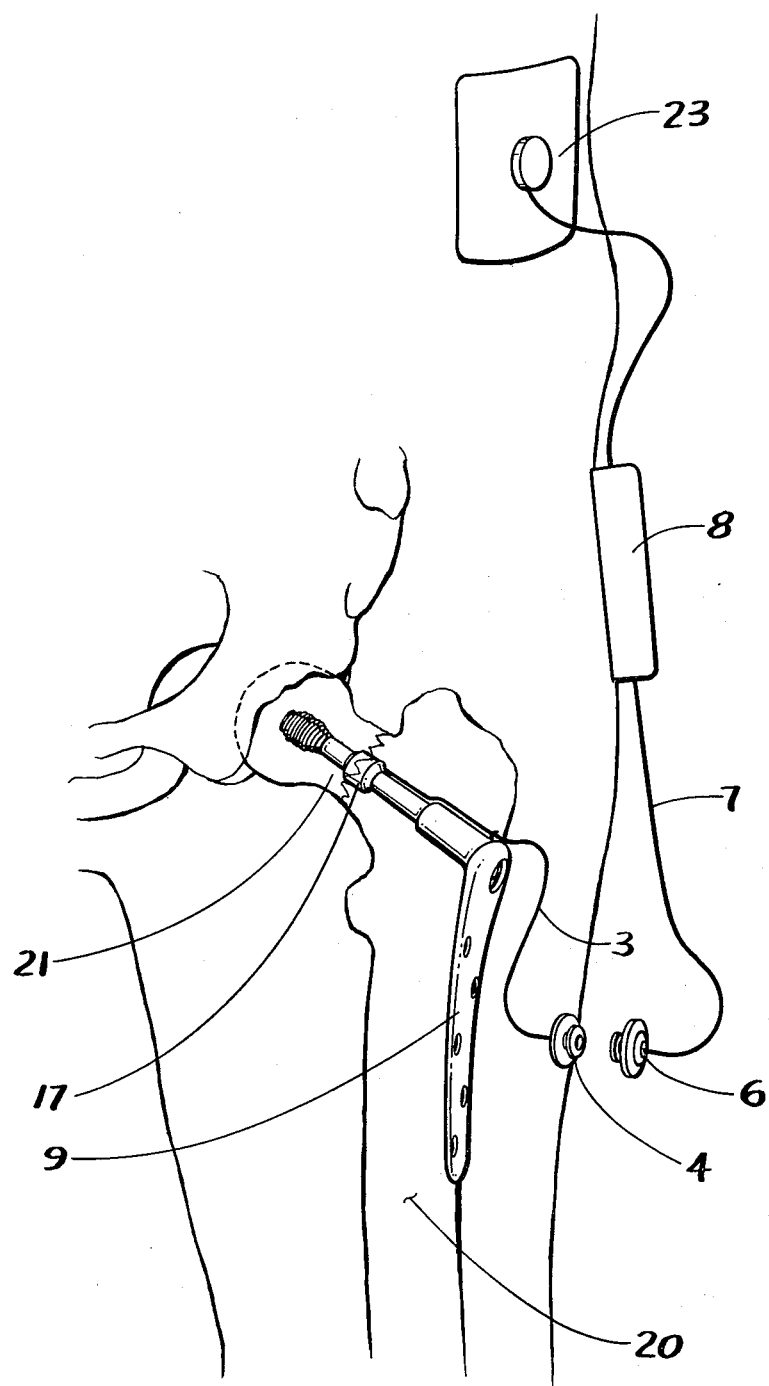
FIG. 2 is a pictoral representation of the cathode assembly in a preferred embodiment in place on a compression hip screw and additionally illustrates the attachment of the cathode assembly to an external current generating stimulator.

Referring now more particularly to the drawings, wherein like numerals represent like elements throughout the several views, FIG. 2 illustrates the use and relationship of one advantageous embodiment of the present invention in the treatment of a fractured femur. A fracture 21 in the neck of femur 20 is reinforced by means of a conventional compression hip screw 9. An electrical stimulation means 8 is attached to a skin surface anode 23 and to an external cable 7 and serves to generate the desired current in the region of the fracture. The osteogenesis stimulation current is transferred to the fracture site through percutaneous connector 4 and magnetic connector 6 and an internal conductor 3. The conductor cable 3 is connected to sleeve assembly 17 which comprises the cathode assembly. While a single conductive cable could lead directly from the electrical stimulating means 8 to the cathode sleeve assembly 17, applicants have found use of the percutaneous skin connector 4 which can be implanted to be advantageous. This quick connection and disconnection of the cathode assembly allows the patient to bathe, but also permits the patient to come for intermittent stimulation eliminating the need for a portable power supply.

Figure 1:
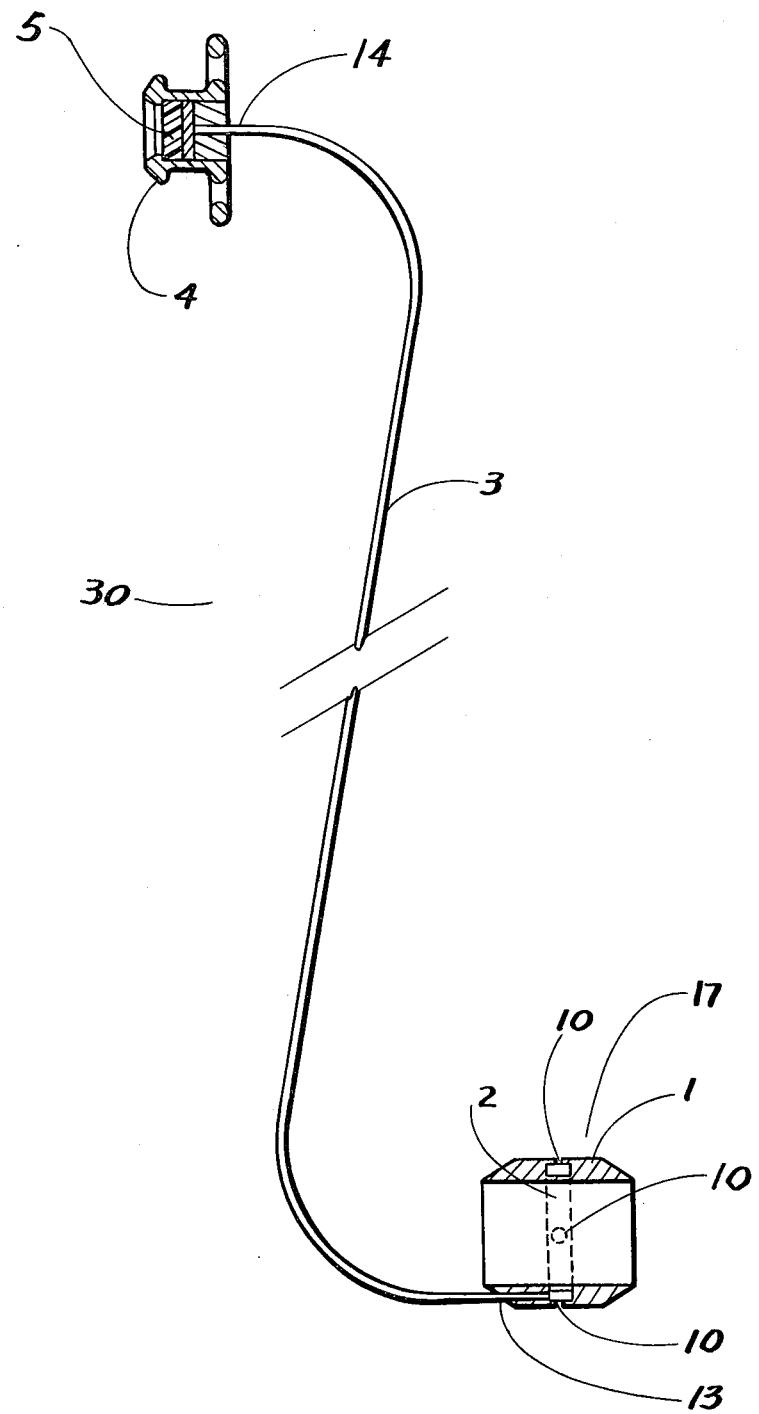
FIG. 1 is a side view, partially in section of the cathode assembly and its associated percutaneous skin connector.

FIG. 1 provides a more detailed view of one embodiment of the sleeve assembly 17 and the percutaneous skin connector 4. In one preferred embodiment, the sleeve assembly 17 is comprised of a tubular carrier made of an insulated material such as polyethylene although it could be made of any other non-conductive implantable material such as silicon, ceramic, etc. In this embodiment, a single ring cathode 2 is provided in the insulative carrier and may be made of any implantable conductive material such as stainless steel, titanium, silver or platinum. As used herein, the terms "implantable" and "biocompatible" are materials which show an acceptable acute and chronic local tissue response. In a preferred embodiment the cathode is made of 316L stainless steel. The cathode is electrically connected to conductive cable 3 which supplies current thereto. The cathode is also encapsulated by the insulated carrier 1 with the exception that there are one or more ports or apertures 10 in the carrier material which permits direct electrical contact from the cathode to the tissues surrounding the carrier. Although the ports 10 can take any form of opening, in a preferred embodiment, the openings are hemispherical in cross-section and circular in plan view. In the embodiment illustrated in FIG. 1, there are four ports equally spaced around a sleeve carrier, each port about 0.41 mm in diameter. An approximately 0.20 mm radius ball end cutter was used to cut through the insulation and into the conductor forming a dimple 0.20 mm in depth. Use of a cylindrical port with no dimple on the cathode has also been effectively utilized. Because the ports have effectively equal electrical resistance to flow, the current supplied to the cathode 2 will be effectively equally distributed among the ports. Therefore, if an external current of 80 microamperes were supplied to cathode 2, 20 microamperes of current will flow out of each of the ports through the surrounding bone tissues.

The number of ports and the amount of current delivered may vary in accordance with the desired electrical stimulation. An optimum current as set forth in the Brighton, et al. patent is between 5 and 20 microamperes at each port site, although different amounts and current densities may be useful for different applications.

Of particular interest is the carrier 1 which in the FIG. 1 embodiment is cylindrical in nature. This can also be seen in different embodiments illustrated in FIGS. 4a and 5a. The center hole in the carrier 1 permits the carrier to be slipped over the screw shaft and pushed into place at the fracture site. The rest of the compression hip screw is then assembled and fastened surgically to the femur 20. The fact that the sleeve assembly 17 is maintained in its required position by the compression hip screw fixation device minimizes the possibility of damage to the cathode and subsequent non-stimulation of osteogenesis or movement of the cathode such that there is a lack of stimulated osteogenesis in the fracture site. The fact that in the compression hip screw embodiment, the cathode and its conductive cable can be inserted in the same hole through which the compression hip screw is assembled, reduces to a minimal degree any independent fracture site trauma. It will be recalled that the prior art cathode techniques would involve either a surgical incision to the external portion of the fracture site and locating a cathode therein or inserting a rigid cathode pin towards the cathode site, both of which involve additional trauma to the fracture site.

One suitable source of 20 microampere current is the Quadpack TM power supply available from Zimmer-.USA, Warsaw, Ind. 46580, listed as item No. 5012-03. A suitable anode pad 23 is also available from Zimmer-.USA and is identified as anode pad part No. 5012-34. In fact, a number of other items and a discussion of prior art procedure in inserting rigid insulated pins and a discussion of treatment is included in the Zimmer brochure, Literature No. B-2360-1, as revised in Sept. 1979, and available from Zimmer.USA, 727 North Detroit Street, P. O. Box 708, Warsaw, Ind. 46580, herein incorporated by reference.

The percutaneous skin connector 4 seen in cross-section in FIG. 1 may be more clearly understood by reference to FIG. 3. Such a connector is discussed in detail in U.S. Pat. No. 4,025,964 issued to Owens on May 31, 1977 entitled "Magnetic Electrical Connectors for Biomedical Percutaneous Implants" and is herein incorporated by reference. Basically, the percutaneous connector illustrated in FIG. 3 includes an enlarged disc-shaped portion 114 with a cylindrical portion 116 extending upward threrefrom. A rim, 118, is integral with the upper end of the cylindrical portion 116 and a magnetic electrical conductor means 5 is secured within the cylindrical portion 116. Cable 3 is electrically connected to the magnetic electrical conductor 5 and facilitates connection to the sleeve assembly 17 as shown in FIG. 1. As shown in FIG. 2, a magnetic connector 6 electrically connected to external cable 7 is magnetically attractible to magnetic electrical conductor 5 when placed in proximity thereto. The magnetic attraction causes connector 6 to come into electrical contact with the magnetic electrical conductor 5 providing an electrical contact and conduction path from external cable 7 through the skin connector to conductive cable 3 with the magnetic force of attraction holding the two connectors together. The apertures illustrated in the disc-shaped portion 114 permit suturing of the skin connector to the patient to prevent dislodging of the connector when the second connector 6 is removed therefrom.

Thus, the present invention also includes a unique method of inseting an osteogenesis-promoting cathode in the vicinity of a fracture site. Although applicable to other internal fixation devices, the method can clearly be understood by reference to FIG. 2 and the compression hip screw embodiment. The screw portion of the compression hip screw device is implanted across the femoral neck fracture by conventional surgical techniques. The sleeve assembly 17 is slipped onto the screw and pushed up the shaft until the sleeve assembly lies across the fracture site 21. The tube and plate portion of the compression hip screw assembly is assembled and fixed to the femur by conventional surgical techniques. The cable leading from the sleeve assembly is looped in the soft tissue with the percutaneous skin connector then being sutured in place at the skin surface. After a short period of time, the patient's skin will grow up around the central cylindrical portion 116 such that the skin is essentially level with the lower edge of rim 118. This method permits precise placement of the cathode without any additional surgical trauma to the patient. By virtue of the physical connection between the sleeve assembly and the screw shaft, the assembly cannot move laterally because it is held in place by the internal fixture device. Effectively, since there are no pressures on it in the axial direction, the cathode assembly will not move in that direction. Although the sleeve assembly does not tend to rotate with respect to the skin tissue around the screw shaft, embodiments can be specifically tailored to prevent rotation on the fixation device. Obviously this method of cathode implantation is useable with other than cylindrical sleeve assemblies, e.g., a dove-tail arrangement between the fixation device and insulating carrier.

In use, the osteogenesis promoting current is delivered from the stimulating means through the various connecting devices to the cathode 2 of the sleeve assembly. Current flows from the cathode through one or more ports in the surrounding bony tissue. The current then flows through other bone and soft tissues to the skin surface anode 23 and from there back to the stimulating means 8.

FIGS. 4a, 4b and 4c, and 5a, 5b and 5c illustrate two alternate embodiments for the sleeve assembly 17. Although both sleeves are designed to fit on a cylindrical shaft, they illustrate a means for preventing rotation of the sleeve assembly about the fixation device. The outer surface 19 of the carrier in FIGS. 4a, 4b and 4c includes a plurality of protruding longitudinal fins which, when the device is mounted on the fixation device with skin and bone tissue surrounding the sleeve assembly, will prevent rotation of the sleeve assembly on the fixation device. In FIGS. 5a, 5b and 5c, there are a plurality of longitudinal flats 16 which perform the same function. Additionally, it is noted that the sleeve embodiment in FIGS. 5a, 5b and 5c, while having the same number of ports, has separate electrical connections to each port, permitting a different amount of current to be supplied to each port. Alternatively, there could be a variation in port size, as illustrated in FIG. 1 in order to provide a variation in current density at the different ports when a single ring cathode is utilized. FIG. 9 illustrates one embodiment in which a multi-cathode sleeve is supplied with current from a plurality of percutaneous skin connectors through their associated conductive cables.

One preferred embodiment of the applicants' invention utilizes a single ring cathode as illustrated in FIGS. 6 and 7 which is connected to cable 3 by any suitable means. In a preferred embodiment, cable 3 is a stainless steel wire 11 which is covered with a Teflon ® coating 12. Two apertures 26 may be made in the cathode strip 2 with the bare end of the stainless steel wire threaded therethrough as shown in FIG. 8.

It is understood that the sleeve assembly 17 need not be cylindrical and may be any tubular shape for fitting around a fixation device. For example, an intramedullary rod may be diamond-shaped, therefore the insulated carrier 1 of the sleeve assembly 17 could be a diamond tubular configuration for slidably fitting onto the intramedullary rod. In fact, it is not necessary for the sleeve assembly to be a tubular shape at all as long as there is some portion of the carrier which is fixable to the fixation device. As previously noted, a dove-tail and groove arrangement would serve to suitably locate the insulated carrier to the fixation device. Furthermore, the insulated carrier could be a solid piece adapted to fit in a recess in a fixation device with the cathode encased therein. The outer surface of the carrier would be exposed to the bone tissue and would contain at least one and preferably a plurality of ports for delivering current to the bone tissue. The outer surface of the carrier preferably would be flush with the outer surface of the fixation device.

Thus, in view of the above teachings, modifications of the cathode assembly will become obvious to those of ordinary skill in the art in view of different fixation devices and different positioning requirements of the cathodes. Different materials from those discussed above can be used as well as different power levels and power supplies in order to meet the requirements of specific applications. Thus, the invention is not limited to the embodiments and applications expressed herein. The cathode assembly described hereinbefore is only limited in accordance with the appended claims.

The embodiments of the invention in which an exclusive property or privilege is claimed are defined as follows:

1. A cathode assembly for use in conjunction with an internal fixation device and a means for supplying current to said cathode for the purpose of stimulating osteogenesis, said means comprising a stimulating means, said assembly comprising:

carrier means for post insertion attachment to said fixation device; and at least one cathode mounted on said carrier means, said carrier means comprising a biocompatible non-conductive material, said carrier means further formed in the shape of a sleeve sized so as to be slidable over at least a portion of said fixation device for mounting thereon.

2. The cathode assembly in accordance with claim 1 wherein said cathode comprises a biocompatible conductive material imbedded in said non-conductive material and said carrier means includes means defining at least one port on an outer surface of said carrier means whereby said at least one port exposes a portion of said cathode.

3. The cathode assembly in accordance with claim 2 wherein said carrier means is cylindrical in shape and has inner and outer cylindrical surfaces.

4. The cathode assembly in accordance with claim 3, wherein said outer cylindrical surface includes means for preventing rotation of said carrier means about said fixation device.

5. The cathode assembly in accordance with claim 4 wherein said carrier means has a longitudinal axis and said means for preventing rotation includes a series of longitudinal flats spaced along said cylindrical surface.

6. The cathode assembly in accordance with claim 4, wherein said carrier means has a longitudinal axis and said means for preventing rotation comprises a series of longitudinal fins spaced on said cylindrical outer surface.

7. The cathode assembly in accordance with claim 1, wherein said carrier means is comprised of polyethylene.

8. The cathode assembly in accordance with claim 1, wherein said cathode is comprised of stainless steel.

9. The cathode assembly in accordance with claim 1, wherein said assembly includes conductive connecting means leading from said stimulating means to said cathode, said conductive connecting means comprising a conductive cable leading from said cathode to said stimulating means.

10. A method of inserting an osteogenesis-promoting cathode in the vicinity of the fracture site wherein an internal fixation device is utilized to stabilize the fracture area, said method comprising the surgical steps of:
   making only the required surgical incision to install the internal fixation device;
   installing at least a portion of the internal fixation device;
   sliding a cathode assembly subsequent to said installing step to a desired position over said at least a portion of the internal fixation device; and
   closing the surgical incision.

11. The method in accordance with claim 10, wherein said internal fixation device is a compression hip screw and said cathode assembly includes a cylindrical carrier slidable over a portion of the compression hip screw, said at least a portion step comprises partially assembling said compression hip screw and said sliding step comprising sliding the cylindrical carrier over the partially assembled compression hip screw until the carrier is located in the vicinity of the fracture site.

12. A cathode assembly for use in conjunction with a compression hip screw and a means for supplying current to said cathode for the purpose of stimulating osteogenesis, said means comprising a stimulating means, said assembly comprising at least one cathode comprised of a biocompatible conductive material;
   carrier means, in the form of a sleeve, for mounting said cathode on said compression hip screw, said carrier means comprising a biocompatible non-conductive material, said biocompatible non-conductive material substantially surrounding said cathode, said carrier means further including means defining ports in an external portion of said carrier means for externally exposing at least a small portion of said cathode.

13. The cathode assembly in accordance with claim 12, wherein said means defining ports defines four ports evenly spaced around the circumference of said sleeved carrier means and said external exposure of said cathode in each port comprises a generally circular area which is 0.41 mm in diameter.

14. A cathode assembly for use in conjunction with a compression hip screw and a means for supplying current to said cathode for the purpose of stimulating osteogenesis, said means comprising a stimulating means, said assembly comprising:
   carrier means for attachment to said compression hip screw; and
   at least one cathode mounted on said carrier means.

15. A method of inserting an osteogenesis-promoting cathode in the vicinity of a fracture site wherein a compression hip screw is utilized to stabilize the fracture area, said method comprising the surgical steps of:
   making only the required surgical incision to install the compression hip screw;
   installing the screw portion of the compression hip screw;
   guiding a cathode assembly to a desired position on the screw portion of said compression hip screw;
   completing the installation of the compression hip screw; and
   closing the surgical incision.

* * * * *